(12) United States Patent
König

(10) Patent No.: US 11,480,538 B2
(45) Date of Patent: Oct. 25, 2022

(54) MEMS GAS SENSOR

(71) Applicant: TDK Corporation, Tokyo (JP)

(72) Inventor: Matthias König, Munich (DE)

(73) Assignee: TDK CORPORATION, Tokyo (JP)

( * ) Notice: Subject to any disclaimer, the term of this patent is extended or adjusted under 35 U.S.C. 154(b) by 286 days.

(21) Appl. No.: 16/649,487

(22) PCT Filed: Aug. 1, 2018

(86) PCT No.: PCT/EP2018/070892
§ 371 (c)(1),
(2) Date: Mar. 20, 2020

(87) PCT Pub. No.: WO2019/057380
PCT Pub. Date: Mar. 28, 2019

(65) Prior Publication Data
US 2020/0240943 A1    Jul. 30, 2020

(30) Foreign Application Priority Data

Sep. 22, 2017  (DE) .......................... 102017122043.7

(51) Int. Cl.
| | |
|---|---|
| *G01N 27/12* | (2006.01) |
| *B81B 7/00* | (2006.01) |
| *B81C 1/00* | (2006.01) |
| *G01N 33/00* | (2006.01) |

(52) U.S. Cl.
CPC ......... *G01N 27/128* (2013.01); *B81B 7/0087* (2013.01); *B81C 1/00261* (2013.01); *G01N 27/123* (2013.01); *G01N 33/0014* (2013.01); *G01N 33/0016* (2013.01); *B81B 2201/0292* (2013.01); *G01N 2291/02863* (2013.01)

(58) Field of Classification Search
CPC ............... G01N 27/128; G01N 27/123; G01N 33/0016; B81B 7/0087; B81B 2201/0292
See application file for complete search history.

(56) References Cited

U.S. PATENT DOCUMENTS

| | | | |
|---|---|---|---|
| 6,326,228 B1 | 12/2001 | Hughes et al. | |
| 10,161,908 B2 | 12/2018 | Moreira Araujo et al. | |
| 10,186,468 B2 | 1/2019 | Pindl et al. | |
| 10,338,021 B2 | 7/2019 | Graunke | |
| 10,347,814 B2 * | 7/2019 | Glacer .................. | H02N 1/006 |
| 2002/0092525 A1 | 7/2002 | Rump et al. | |
| 2015/0177171 A1 * | 6/2015 | Kim ..................... | G01N 27/128 |
| | | | 73/31.05 |

FOREIGN PATENT DOCUMENTS

| | | |
|---|---|---|
| DE | 19708770 C1 | 8/1998 |
| DE | 19911867 A1 | 10/2000 |
| | (Continued) | |

OTHER PUBLICATIONS

Odita, M., et al., "Ga2O3 thin films for high-temperature gas sensors," Applied Surface Science, vol. 142, Apr. 1999, pp. 188-191.

*Primary Examiner* — David Z Huang
(74) *Attorney, Agent, or Firm* — Slater Matsil, LLP

(57) ABSTRACT

A MEMS gas sensor is disclosed. In an embodiment a MEMS gas sensor includes a carrier having a recess, a gas sensitive element arranged in the recess and a shielding layer at least partially covering the recess.

14 Claims, 7 Drawing Sheets

(56) References Cited

FOREIGN PATENT DOCUMENTS

| DE | 102017204944 A1 | 9/2017 |
|----|-----------------|--------|
| DE | 102017102188 A1 | 10/2017 |
| DE | 102017205539 A1 | 10/2017 |
| EP | 3139159 A1 | 3/2017 |
| JP | 2014081367 A | 5/2014 |
| WO | 2015121312 A1 | 8/2015 |

* cited by examiner

MEMS GAS SENSOR

This patent application is a national phase filing under section 371 of PCT/EP2018/070892, filed Aug. 1, 2018, which claims the priority of German patent application 102017122043.7, filed Sep. 22, 2017, each of which is incorporated herein by reference in its entirety.

TECHNICAL FIELD

The present invention concerns a MEMS gas sensor.

BACKGROUND

MEMS gas sensors have attracted much interest because of their potential to be usable in mass markets, e.g., mobile phones or air quality home stations. However, a disadvantage of these sensors is their high power consumption.

Odita, M et al. "Ga2O3 thin films for high-temperature gas sensors", Applied Surface Science 142.1 (1999): 188-191 discloses an example of a working principle of a MEMS gas sensor. In particular, the MEMS gas sensor comprises a metal oxide layer on a ceramic substrate which is heated to a working temperature.

Other types of MEMS gas sensors are also possible.

SUMMARY OF THE INVENTION

Embodiments provide an improved MEMS gas sensor. Further embodiments provide a MEMS gas sensor with a reduced power consumption.

A MEMS gas sensor is provided which comprises a carrier having a recess, a gas sensitive element which is arranged in the recess, and a shielding layer which at least partially covers the recess.

The shielding layer may be configured to reduce a heat transfer away from the gas sensitive element. In particular, the shielding layer may be configured to reduce a heat transfer by convection and radiation.

The shielding layer may completely cover the recess except for ventilation holes penetrating the shielding layer. Thus, the shielding layer may prevent that heat that is emitted by the gas sensitive element may dissipate from the recess to an environment of the MEMS gas sensor. In particular, the shielding layer may be configured to partially reflect infrared electromagnetic radiation emitted by the gas sensitive element. The shielding layer may also be configured to emit heat into the recess in response to being heated up by the heat from the gas sensitive element. Thus, the shielding layer may ensure that not all of the heat emitted by the gas sensitive element is lost to the environment.

When a gas molecule abuts the gas sensitive element, the gas molecule may be burnt, wherein the end products of the burning process may be in contact with the other gas molecules in the recess and may transfer heat to these gas molecules. Thereby, an equilibrium between educts and products can be achieved.

In this context "heat" may in particular correspond to electromagnetic radiation in the infrared spectrum. "Heat" may also correspond to electromagnetic radiation in other frequency spectra. However, the terms "heat" and "heat transfer" may also refer to mechanisms of heat transfer other than radiation, for example, convection.

The gas sensitive element may be an element which allows to detect one or more types of gas. For example, the gas sensitive element may be a metal oxide layer. Other types of gas sensitive elements are also possible. For example, the gas sensitive element may be a pellistor or a metaloxide semiconductor gas sensor. Typically, the gas sensitive element has to be heated up to a working temperature, which may be in the range of 200° C. to 1200° C. For example, the working temperature may be 600° C.

The recess in the carrier may form a chamber, in which the gas sensitive element is exposed to a gas which shall be measure by the gas sensitive element.

The carrier on which the gas sensitive element is arranged may be constructed to have a small volume. In particular, a membrane on which the gas sensitive element can be arranged may be thin such that the membrane has a low heat capacity.

As discussed above, the shielding layer may reduce the heat dissipating from the gas sensitive element to the environment. Thus, less power has to be applied to the gas sensitive element in order to keep the gas sensitive element at its stable working temperature. Accordingly, the shielding layer may reduce the power consumption of the MEMS gas sensor.

Moreover, the shielding layer may also form a mechanical support structure which may help to improve the mechanical stability of the MEMS gas sensor. Thereby, the arrangement of the shielding layer may allow the construction of thinner membranes which absorb less heat. In a MEMS gas sensor without a shielding layer, there is a lower limit of the thickness of the membrane because the MEMS gas sensor should be constructed such that it has a mechanical stability sufficient to withstand a drop test. When the mechanical stability is provided by the shielding layer, use of thinner membranes becomes possible.

The design of the shielding layer may allow to adjust the sensor speed and the power consumption of the sensor in a desired manner. In particular, by modifying the size and the density of ventilation holes penetrating through the shielding layer, the sensor speed and the power consumption can be optimized.

The MEMS gas sensor may be configured to heat the gas sensitive element. In particular, the sensor may be configured to heat the gas sensitive element to its working temperature. The working temperature may be in the range of 200° C. to 1200° C., for example, 600° C. For heating the gas sensitive element, power has to be consumed by the MEMS gas sensor. In order to keep the power consumption to an acceptable limit, the present invention reduces heat dissipation.

The shielding layer may be configured to reflect heat emitted by the gas sensitive element. The heat reflected by the shielding layer may remain in the recess and may, thus, heat up the gas sensitive element. Thereby, the shielding layer reduces the heat loss due to radiation. The shielding layer also reduces the heat loss by convection as the shielding layer may prevent molecules that have been heated up to escape from the recess.

According to one embodiment, the shielding layer may consist of a single layer. The material of the layer shall be chosen such that it does not emit heat and that it is a good reflector, i.e., that it does not absorb heat to a large extent.

In an alternative embodiment, the shielding layer comprises at least a lower layer which faces towards the gas sensitive element and an upper layer which faces away from the gas sensitive element. In this embodiment, the lower layer can be optimized to reflect heat emitted by the gas sensitive element. The upper layer can be optimized not to emit heat to an environment of the MEMS gas sensor.

The lower layer may have an absorptance of less than 0.4. Accordingly, the lower layer may not absorb much of the heat emitted by the gas sensitive element.

In this context, "absorptance" may be defined as the fraction of incident electromagnetic power that is absorbed at an interface. The absorptance may be defined as the ratio of a radiant flux absorbed by a surface to the radiant flux received by that surface. A white body has an absorptance of zero. The lower layer of the shielding layer may be designed to resemble the ideal white body.

The lower layer may comprise aluminum, silver or palladium. The lower layer may also consist of one of these materials. Each of these materials provides the desired low absorptance. Therefore, each of these materials is particularly suitable for the lower layer.

The upper layer may have an emissivity of less than 0.4. Accordingly, the upper layer may be configured not to emit much heat to the environment.

The emissivity may provide information about an effectiveness of the upper layer in emitting energy as thermal radiation. The emissivity may be defined as the ratio of an energy radiated by a surface to the energy radiated by a black body at the same temperature.

The upper layer may comprise cadmium, tungsten or bronze. Each of these materials is configured to provide the desired low emissivity. The upper layer may also consist of one of these materials.

Further, the shielding layer may comprise a middle layer which is sandwiched between the lower layer and the upper layer. The middle layer may be configured to reduce a thermal conduction between the lower layer and the upper layer. Accordingly, the middle layer shall prevent that heat is traveling from the bottom of the shielding layer to an upper surface of the shielding layer. Moreover, the middle layer may also help to improve the mechanical stability of the shielding layer. Preferably, the middle layer comprises an oxide, for example, aluminum oxide or silicon oxide as these materials have a low thermal conductivity. In some embodiments, mechanical stress due to different thermal expansion coefficients shall be prevented. In these embodiments, the middle layer may consist of or comprise titanium.

The shielding layer may be penetrated by ventilation holes. The ventilation holes may enable gas from the environment to enter into the recess and thus to be measured by the gas sensitive element. By varying the size and the density of the ventilation holes, it is possible to adjust the speed and the power consumption of the sensor.

The MEMS gas sensor may comprise a bottom shielding layer which is arranged on the side of the carrier facing away from the gas sensitive element. The MEMS gas sensor may comprise a lateral shielding layer which is arranged laterally to the gas sensitive element. Accordingly, the MEMS gas sensor can be encapsulated by the shielding layer, the lateral shielding layer and the bottom shielding layer. The lateral shielding layer reduces the heat loss to the lateral sides of the carrier. The bottom shielding layer may reduce the heat loss at the bottom of the carrier.

The MEMS gas sensor may comprise multiple shielding layers which at least partially cover the recess and which are layered on each other. By forming multiple layers of shielding layers, the heat loss can be reduced further.

The gas sensitive element may be fixed to the carrier by spring arms. In particular, the spring arms may have a meander shape, wherein the gas sensitive element is in direct mechanical contact with the carrier only via the spring arms. Accordingly, the gas sensitive element may not be in contact with the carrier over a large surface. Thereby, a heat loss due to thermal conduction from the gas sensitive element to the carrier can be minimized.

BRIEF DESCRIPTION OF THE DRAWINGS

In the following, the present invention is discussed with respect to the drawings.

DETAILED DESCRIPTION OF ILLUSTRATIVE EMBODIMENTS

Figure 1:
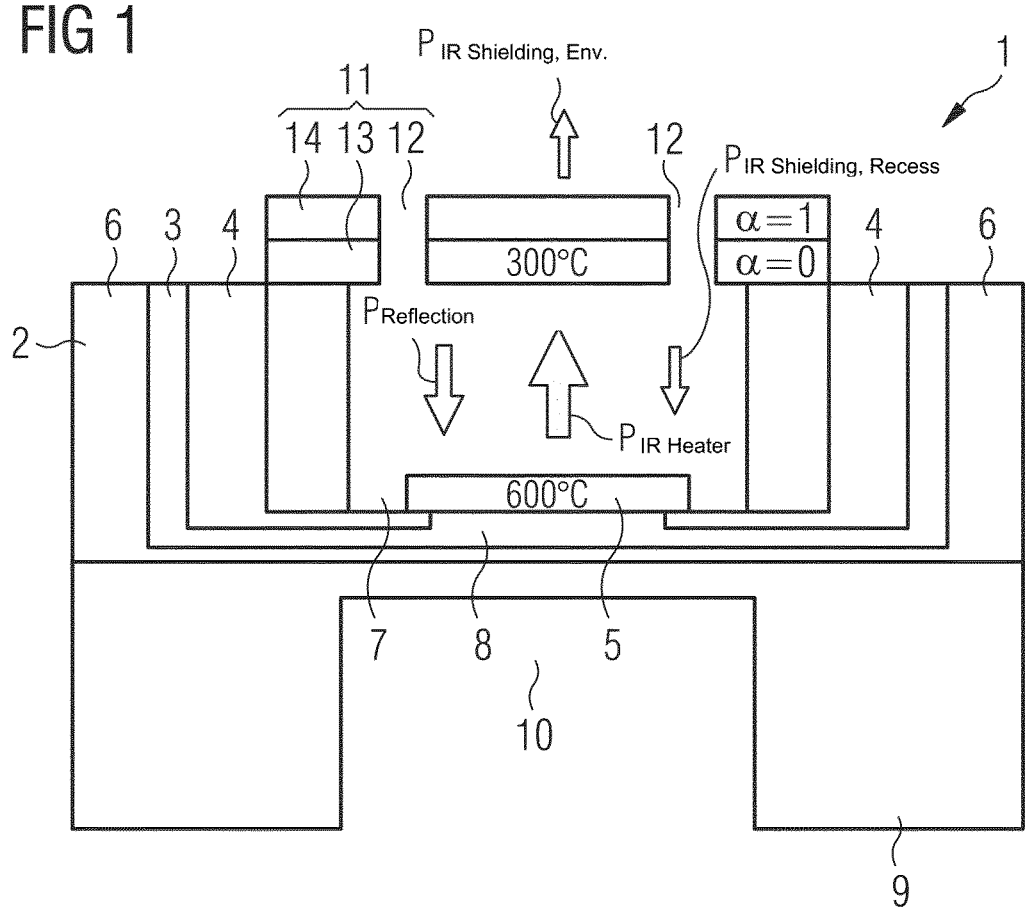
FIG. 1 schematically shows a MEMS gas sensor.

FIG. 1 schematically shows a MEMS gas sensor 1. The MEMS gas sensor 1 comprises a carrier 2. The carrier 2 comprises an isolation 3 and metallic structures. The metallic structures in the carrier form sensing contacts 4 which are in direct contact with a gas sensitive element 5. The sensing contacts 4 allow reading out the measurement data obtained by the gas sensitive element 5. The metallic structures further comprise heater contacts 6 which are configured to be connected to a heating element and which are used to heat the carrier 2 and, thereby, the gas sensitive element 5.

Further, a recess 7 is formed in the carrier 2. In the recess 7, the gas sensitive element 5 is arranged. The gas sensitive element 5 comprises a gas sensitive layer, e.g., a metal oxide layer.

Below the recess 7, the carrier 2 comprises a thinned area. The thinned area of the carrier forms a membrane 8. The gas sensitive element 5 is arranged on the membrane 8.

The MEMS gas sensor 1 is configured to heat the gas sensitive element 5 via the heater contacts 6. To enable a stable operation of the gas sensitive element 5, the gas sensitive element 5 has to be heated to a working temperature. The working temperature depends on different factors, in particular the material of the gas sensitive element 5 and the measurement principle of the MEMS gas sensor 1. The working temperature can be in the range of 200° C. to 1200° C.

The carrier 2 is arranged on a substrate 9 which may comprise silicon. The substrate 9 comprises an opening 10 which is arranged below the membrane 8.

Moreover, the MEMS gas sensor 1 comprises a shielding layer 11 which at least partially covers the recess 7 in the carrier 2. The shielding layer 11 is configured to reduce or eliminate a transfer of heat from the gas sensitive element 5 to an environment of the MEMS gas sensor 1. When less heat is transferred from the gas sensitive element 5 to the environment, less heat has to be applied to the gas sensitive element 5 to maintain its working temperature and, thus, the power consumption of the MEMS gas sensor 1 is reduced. Heating the gas sensitive element 5 is an important factor in the power consumption of the MEMS gas sensor 1.

Heat is transferred from the gas sensitive element 5 to the environment of the MEMS gas sensor 1 by three mechanisms: radiation, convection and thermal conduction.

Thermal conduction is the transfer of thermal energy through matter. In particular, thermal conduction is the transfer of heat by microscopic collisions of particles and movement of electrons within a body. The shielding layer 11 does not affect a heat loss due to thermal conduction. However, as discussed later with respect to the sixth embodiment, the MEMS gas sensor 1 can further comprise means to reduce a heat loss due to thermal conduction.

Radiation corresponds to heat being emitted by the gas sensitive element 5 as electromagnetic radiation. The heat that is emitted by the gas sensitive element 5 corresponds to electromagnetic radiation in a wide variety of frequencies. In particular, the heat emitted by the gas sensitive element 5 is electromagnetic radiation in the infrared frequency range. The shielding layer 11 can at least partially reflect the emitted electromagnetic radiation, thereby preventing that it dissipates to the environment.

Convection is the heat transfer due to bulk movement of molecules. Convection takes place through advection, diffusion or both. The gas sensitive element 5 heats up the gas molecules in the recess 7. The shielding layer 11 forms a lid on the recess 7, thereby significantly reducing the number of gas molecules that leave the recess 7. The shielding layer 11 slows down the gas exchange between the recess 7 and the environment. Thus, the shielding layer 11 slows down the heat loss due to convection as the molecules that have been heated remain longer in the recess 7.

The shielding layer 11 does not completely seal the recess 7 as otherwise no gas exchange between the recess 7 and the environment of the MEMS gas sensor 1 would be possible. In this case, the gas sensitive element 5 could not measure the gas from the environment. Thus, ventilation holes 12 are arranged in the shielding layer 11. The ventilation holes 12 penetrate through the shielding layer 11. Thereby, the ventilation holes 12 allow gas from the environment to enter into the recess 7. The shielding layer 11 may cover the recess 7 completely, except for the ventilation holes 12.

By choosing the diameter and the density of the ventilation holes 12, it is possible to optimize the speed and the power consumption of the MEMS gas sensor 1.

In FIG. 1, the heat transfer between the gas sensitive element 5, the shielding layer 11 and the environment is indicated by arrows. The gas sensitive element 5 emits heat into the recess 7 as indicated by an arrow $P_{IR,Heater}$. The arrow $P_{IR,Heater}$ includes heat transferred by radiation and by convection.

The lower surface of the shielding layer 11, which faces towards the recess 7, partially reflects the heat radiated into the recess 7 by the gas sensitive element 5. Moreover, the shielding layer 11 also prevents that gas molecules that have been heated escape from the recess 7 as the molecules bounce back into the recess 7 after colliding with the shielding layer 11. An arrow $P_{Reflection}$ indicates the heat that has been reflected by the shielding layer 11 back into the recess 7.

The shielding layer 11 also partially absorbs the heat emitted by the gas sensitive element 5. The absorbed heat is emitted by the shielding layer 11 partially back into the recess 7 and partially to the environment. An arrow $P_{IR,Shielding,Recess}$ pointing into the recess 7 indicates the heat that is emitted by the shielding layer 11 into the recess 7. An arrow $P_{IR,Shielding,Env.}$ pointing away from the recess indicates the heat that is emitted by the shielding layer 11 into the environment. The heat that is emitted to the environment is dissipated and lost.

Without the shielding layer 11, the heat loss would be determined only by arrow $P_{IR,Heater}$. The addition of the shielding layer 11 reduces the heat loss as heat is transferred back to the gas sensitive element 5 as indicated by arrows $P_{Reflection}$ and $P_{IR,Shielding,Recess}$. Only the heat indicated by arrow $P_{IR,Shielding,Env.}$ dissipates to the environment.

In other words, the shielding layer 11 can ensure that not all of the heat emitted by the gas sensitive element 5 into the recess 7 is dissipated to the environment. Instead, heat is reflected back to the gas sensitive element 5 and emitted back into the recess 7 by the shielding layer 11, thereby significantly reducing the heat loss and, thus, the power consumption of the MEMS gas sensor 1.

The shielding layer 11 comprises two sublayers. In particular, the shielding layer 11 comprises a lower layer 13 which faces towards the recess 7 and an upper layer 14 which faces away from the recess 7. This design of the shielding layer 11 allows optimizing the material of the lower layer 13 such that it does not absorb a lot of energy and/or the material of the upper layer 14 such that it does not emit a lot of heat.

The material of the lower layer 13 is chosen such that the lower layer 13 resembles a white body. A white body is an idealized physical body which reflects all incident radiation completely and uniformly in all directions. In particular, the material of the lower layer 13 is highly reflecting with respect to infrared radiation emitted by the gas sensitive element 5. The lower layer 13 may comprise at least one of aluminum, silver or palladium. The lower layer 13 may also consist of one of these materials.

The material of the upper layer 14 is chosen such that the upper layer 14 does not emit much heat to the environment. The upper layer 14 preferably comprises or consists of cadmium, tungsten or bronze.

Further, the carrier 2 and, in particular, the membrane 8 are designed such that they have a small volume. Thereby, it can be ensured that the carrier 2 and, in particular, the membrane 8 have a small heat capacity, i.e., that a small amount of heat being transferred to the carrier 2 results in a large temperature change. Thus, not too much energy or heat is required to heat up the membrane 8.

However, as a drawback, the membrane 8 is not very stable mechanically. Thus, it may be questionable if the MEMS gas sensor 1 can withstand a drop test as the membrane 8 may be bend strongly in a drop test and may even be destroyed thereby.

The shielding layer 11 provides sufficient mechanical stability to the MEMS gas sensor 1. The shielding layer 11 is fixed to the membrane 8. The shielding layer 11 functions as a support structure for the membrane 8 which ensures that the membrane 8 is not bend excessively during a drop test. Thus, the shielding layer 11 ensures that the MEMS gas sensor 1 withstands the drop test.

To further improve mechanical stability, the shielding layer 11 may have a particular stable design. The shielding layer 11 may have a T-shaped or H-shaped cross-section when seen in a direction perpendicular to a surface normal of the shielding layer 11. Such a cross section provides a high mechanical stability with a rather small volume. For example, steel beams are also formed in this shape. A small volume of the shielding layer 11 is desirable as it corresponds to a small heat capacity and conductivity of the shielding layer 11.

Figure 2:
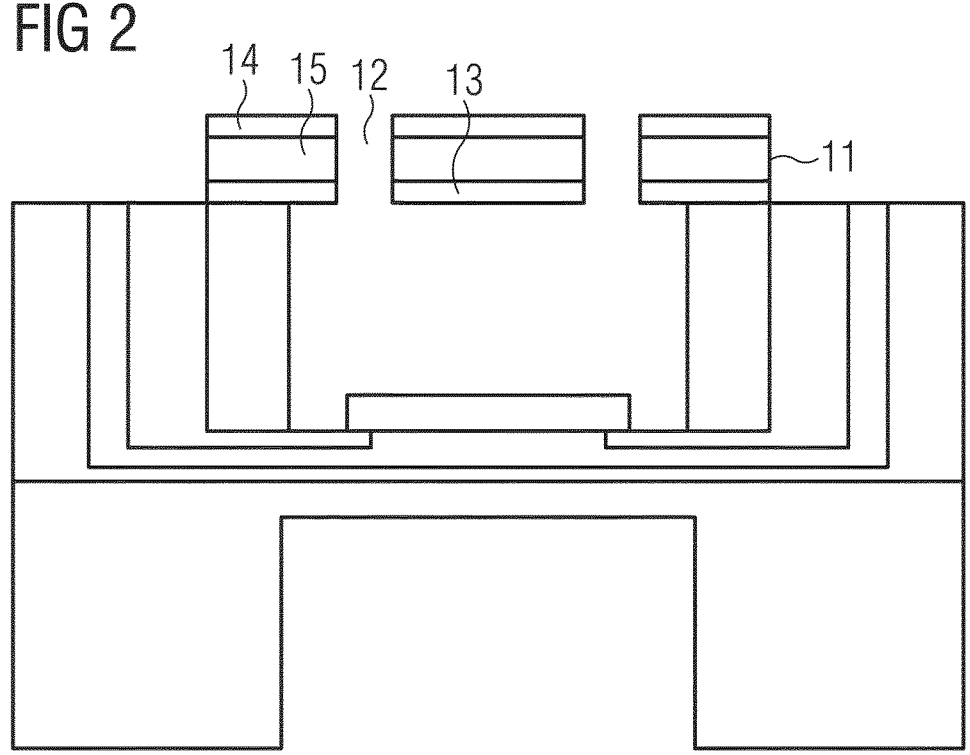
FIG. 2 shows a second embodiment of the MEMS gas sensor.

FIG. 2 shows a second embodiment of the MEMS gas sensor 1. The second embodiment differs from the first embodiment in that the shielding layer 11 comprises three sublayers. The shielding layer 11 comprises the lower layer 13 as discussed with respect to the first embodiment and the upper layer 14 as discussed with respect to the first embodiment. Further, the shielding layer 11 comprises a middle layer 15 which is sandwiched between the lower layer 13 and the upper layer 14.

The middle layer 15 reduces the thermal conduction between the lower layer 13 and the upper layer 14. Thus, the middle layer 15 helps to further reduce the heat emitted by the upper layer 14 to the environment as less heat is transferred by thermal conduction from the lower layer 13 to the upper layer 14. Moreover, the middle layer 15 can help to provide further mechanical stability to the shielding layer 11. The middle layer 15 may consist of or comprise at least one of aluminum oxide, silicon oxide and titanium.

Figure 3:
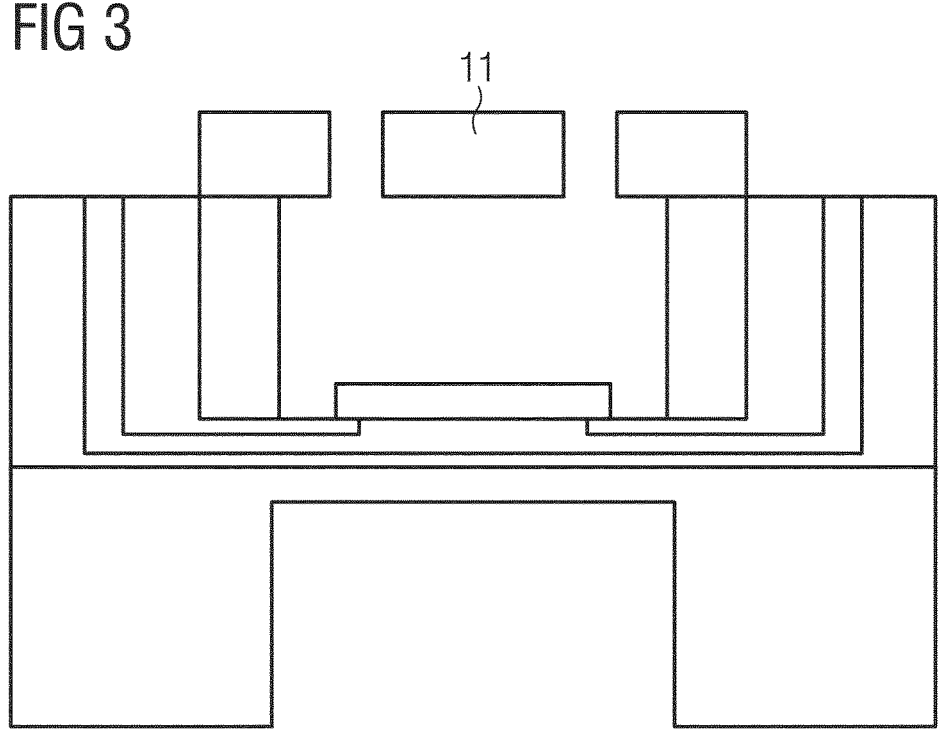
FIG. 3 shows a third embodiment of the MEMS gas sensor.

FIG. 3 shows a third embodiment of the MEMS gas sensor 1. According to the third embodiment, the shielding layer 11 consists of a single layer.

Figure 4:
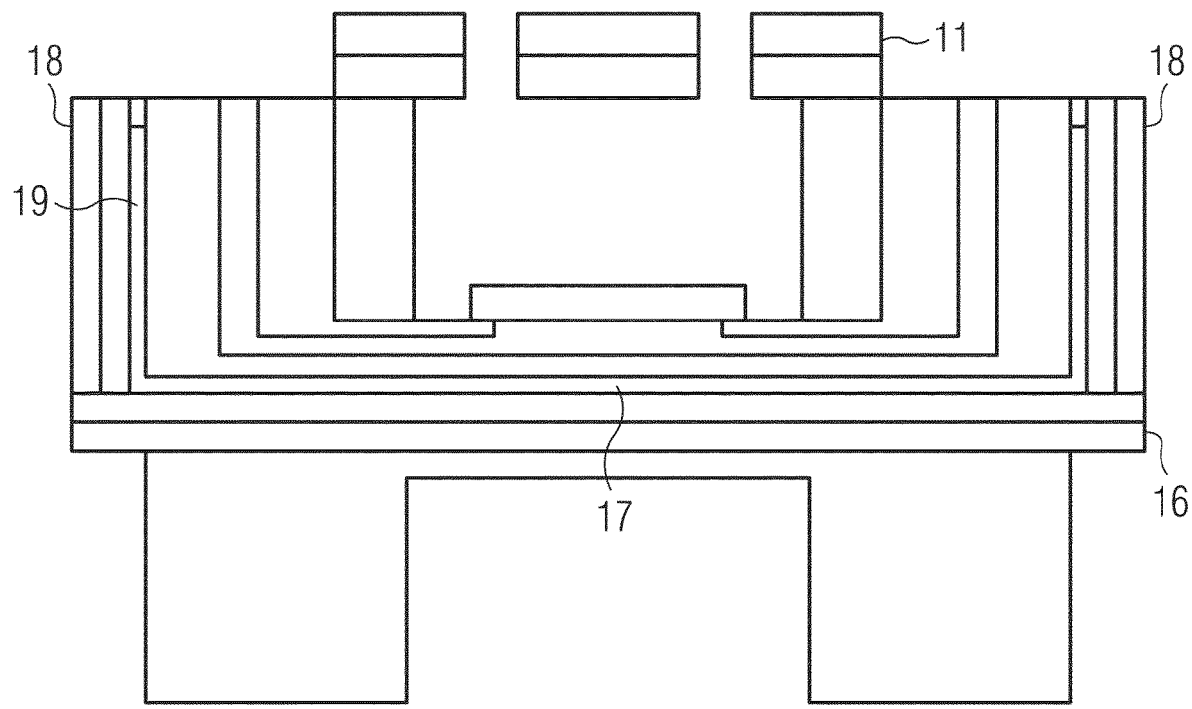
FIG. 4 shows a fourth embodiment of the MEMS gas sensor.

FIG. 4 shows a fourth embodiment of the MEMS gas sensor 1. According to the fourth embodiment, the MEMS gas sensor 1 comprises a bottom shielding layer 16 which is arranged on the side of the carrier 2 facing away from the gas sensitive element 5. Of course, the gas sensitive element 5 does not only emit heat into the recess 7 but also into other directions. In particular, the gas sensitive element 5 also emits heat to the carrier 2. By arranging the bottom shielding layer 16 below the carrier 2, the heat loss to the environment by heat emitted from the carrier 2 to the environment can be reduced significantly.

The bottom shielding layer 16 and the carrier 2 are separated by a gap 17. The gap 17 comprises a vacuum, i.e., air from the gap 17 has been evacuated. Thus, heat convection from the carrier 2 to the bottom shielding layer 16 can be avoided or at least reduced. In an alternative embodiment, the bottom shielding layer 16 abuts the carrier 2.

Moreover, the MEMS gas sensor 1 comprises lateral shielding layers 18. The lateral shielding layers 18 are arranged on the lateral side faces of the carrier 2. The lateral shielding layers 18 and the carrier 2 are also separated by a gap 19. The gap 19 also comprises a vacuum, i.e., air from the gap 19 has been evacuated. Thus, heat convection from the carrier 2 to the lateral shielding layers 18 can be avoided or at least reduced. In an alternative embodiment, the lateral shielding layers 18 abut the carrier 2.

The carrier 2 can be encapsulated by the shielding layer 11, the lateral shielding layers 18 and the bottom shielding layer 16. Only the ventilation holes 12 in the shielding layer 11 penetrate through the encapsulation.

Figure 5:
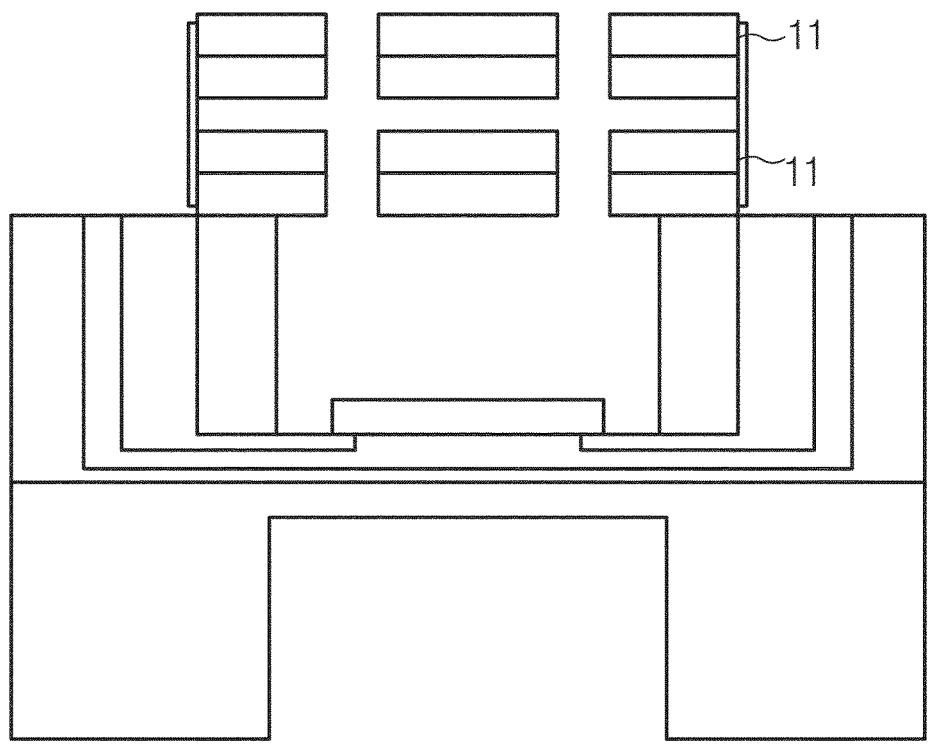
FIG. 5 shows a fifth embodiment of the MEMS gas sensor.

FIG. 5 shows a fifth embodiment of the MEMS gas sensor 1. According to the fifth embodiment, the MEMS gas sensor 1 comprises multiple shielding layers 11 which form a layered structure. The layered arrangement of multiple shielding layers 11 further reduces heat loss.

Figure 6:
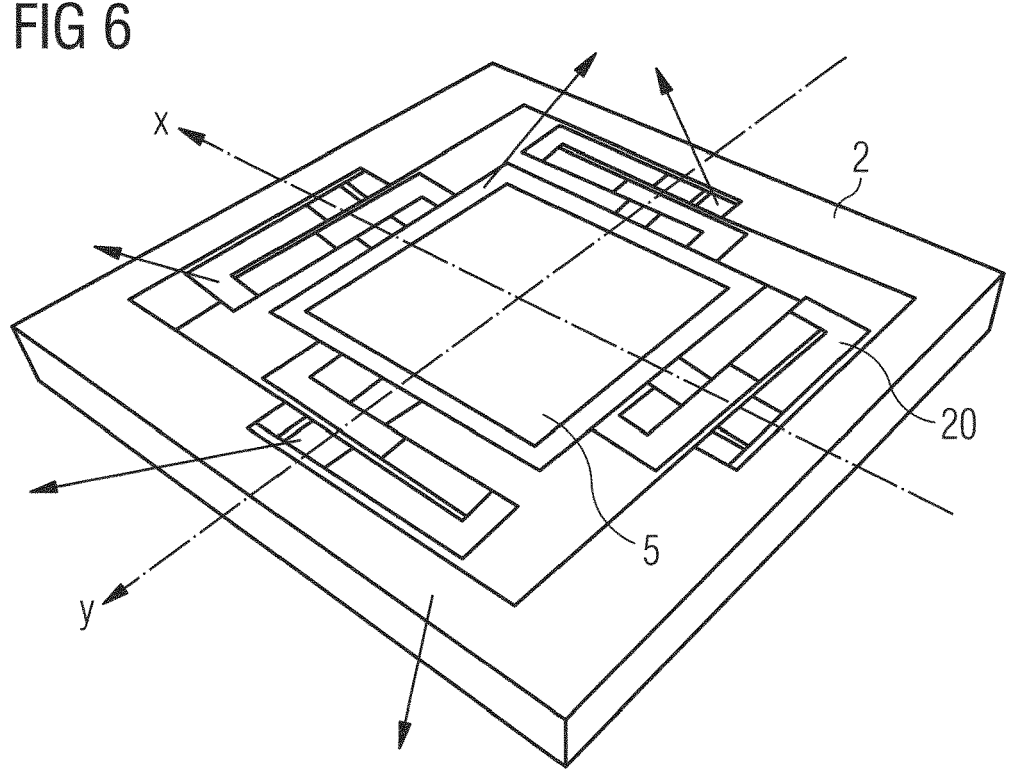
FIG. 6 shows a sixth embodiment of the MEMS gas sensor.

FIG. 6 shows a sixth embodiment of the MEMS gas sensor 1. In the sixth embodiment, the gas sensitive element 5 is fixed to the carrier 2 by spring arms 20. The spring arms 20 have a meander shape. A thermal coupling between the gas sensitive element 5 and the carrier 2 occurs only via the spring arms 213. This reduces heat loss by thermal conduction as less heat is transferred by thermal conduction from the gas sensitive element 5 to the carrier 2. Further the MEMS gas sensor 1 according to the sixth embodiment comprises a shielding layer 11, which is not shown in FIG. 6.

The first to sixth embodiment can be combined. In particular, the shielding layer 11 of the first embodiment may be replaced by a shielding layer having another substructure as disclosed with respect to the second and third embodiment. Additionally or alternatively, the bottom shielding layer 16, the lateral shielding layer 18 and/or the spring arms 20 may be added to the first embodiment.

FIGS. 7 to 13 show a first method of manufacturing the MEMS gas sensor 1 of the first embodiment. According to the first method, the MEMS gas sensor 1 is manufactured by wafer-to-wafer bonding.

Figure 7:
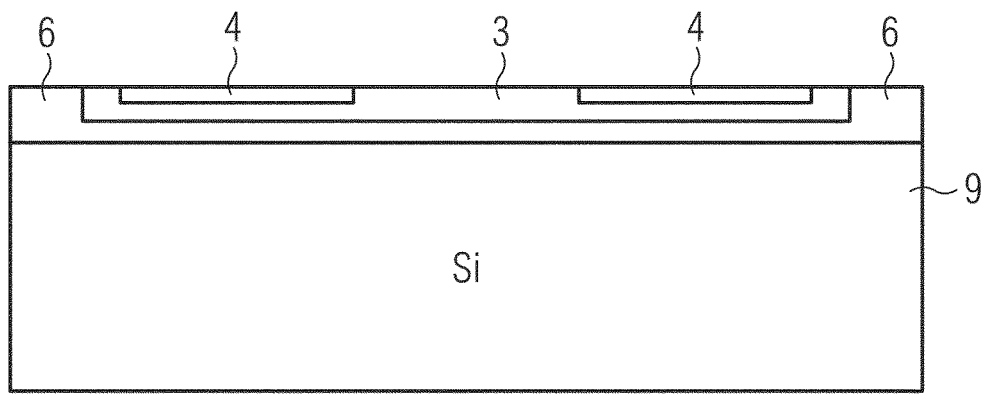
FIGS. 7 to 13 show a method of manufacturing the MEMS gas sensor using wafer-to-wafer bonding.
Figure 8:
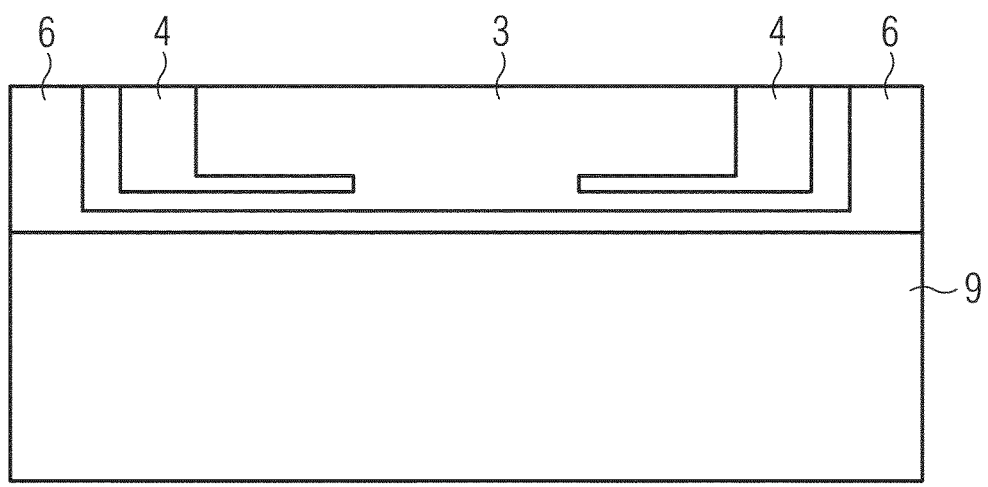

In a first step, shown in FIGS. 7 and 8, the carrier 2 is formed on the silicon substrate 9 by applying the isolation 3 and the metallic structure for the heater contacts 6 and the sensing contacts 4. This step is performed on wafer-level. Thus, a multitude of MEMS gas sensors 1 is manufactured simultaneously. FIGS. 7 and 8 show a small part of a first wafer.

Figure 9:
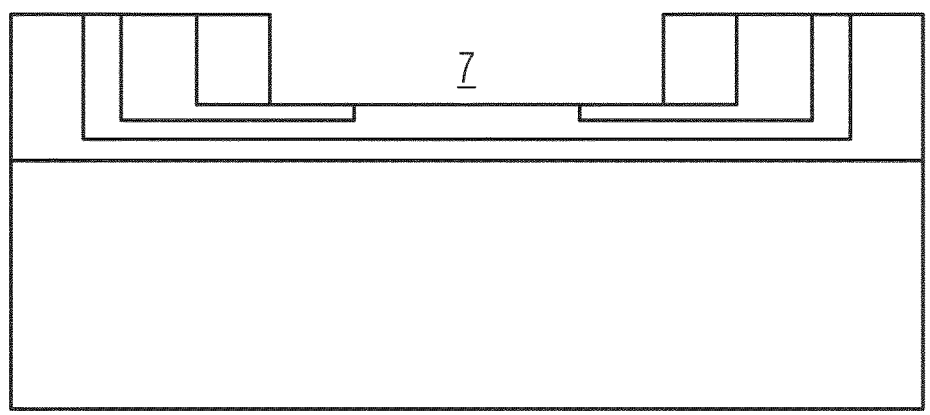
Figure 10:
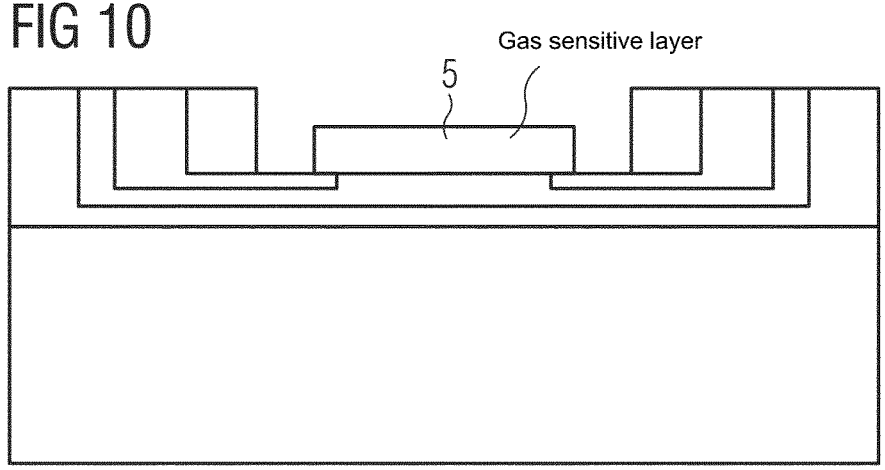

In a next step, shown in FIG. 9, the recess 7 is formed by trench etching. In a next step, shown in FIG. 10, the gas sensitive element 5 is dispensed in the recess. The gas sensitive element 5 may also be formed by other methods.

Figure 11:
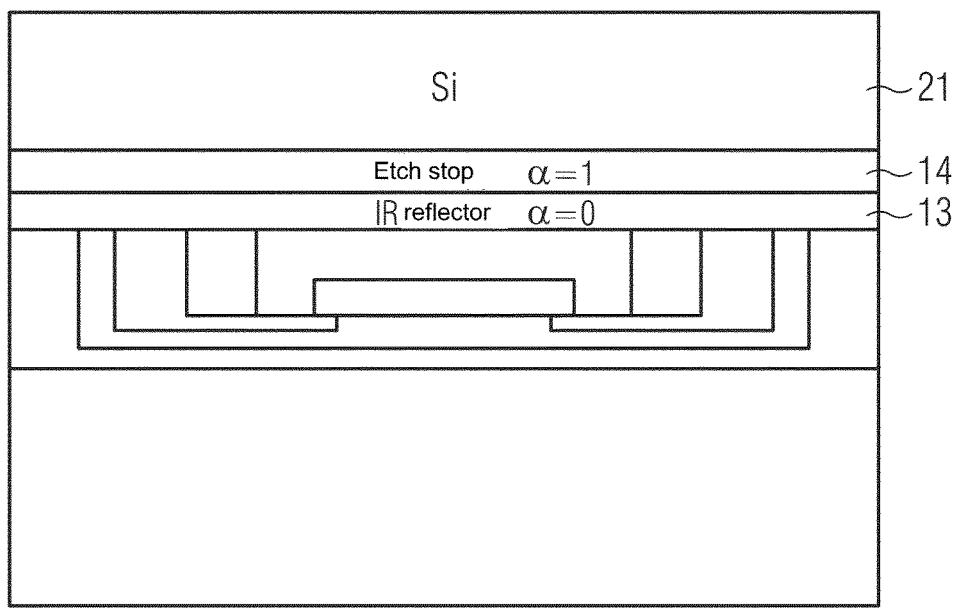

In a next step, shown in FIG. 11, a second wafer is bonded to the first wafer. The second wafer comprises a layered structure with a lower layer 13 facing towards the carrier 2, an upper layer 14 arranged on the lower layer 13 and a silicon layer 21 which will be removed later. The lower layer 13 corresponds to the lower layer 13 of the shielding layer 11. The upper layer 14 corresponds to the upper layer 14 of the shielding layer 11.

Figure 12:
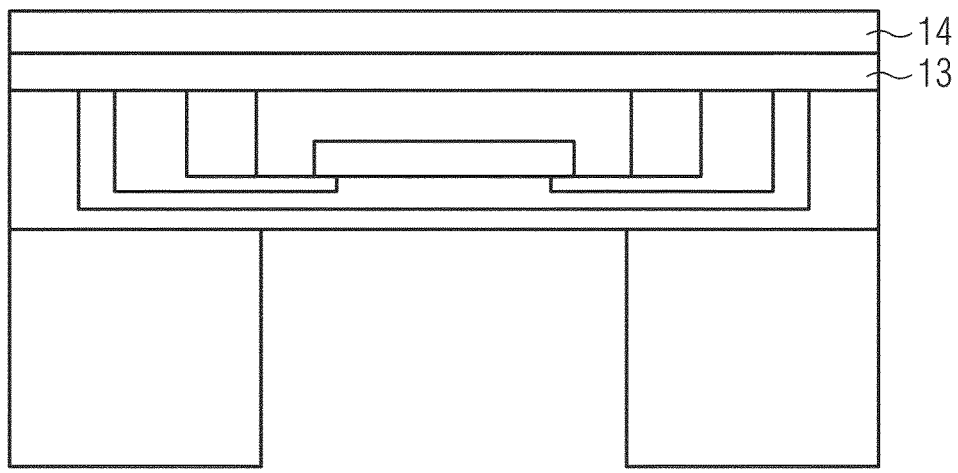

In a next step, shown in FIG. 12, the silicon layer 21 of the second wafer is removed, for example, by etching or polishing. Further, the opening 10 is formed in the silicon substrate 9 below the membrane 8. The opening 10 may be formed by etching.

Figure 13:
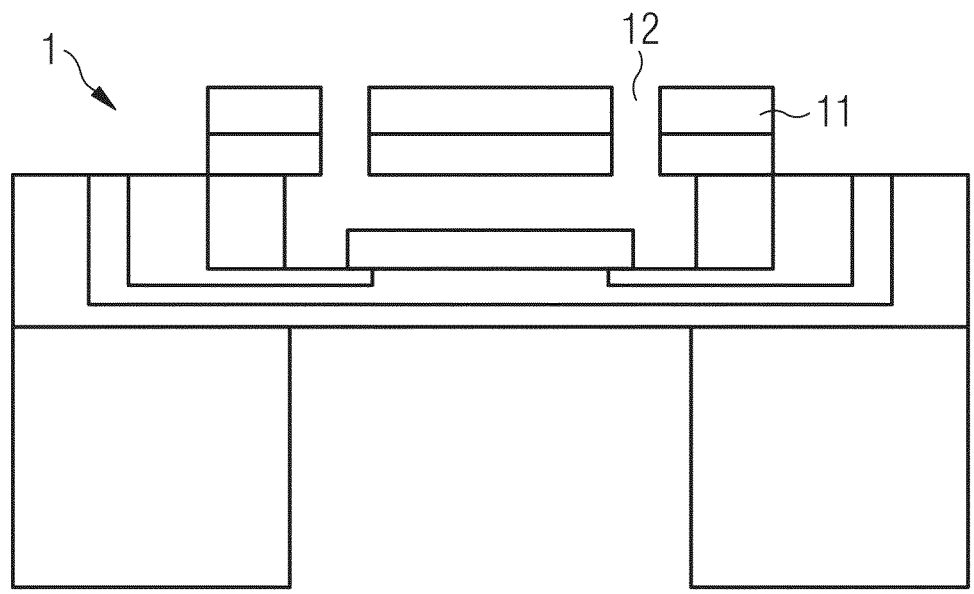

In a last step, shown in FIG. 13, the ventilation holes 12 are formed in the shielding layer 11. Moreover, the shielding layer 11 is partly removed on parts which do not cover the recess 7.

Figure 14:
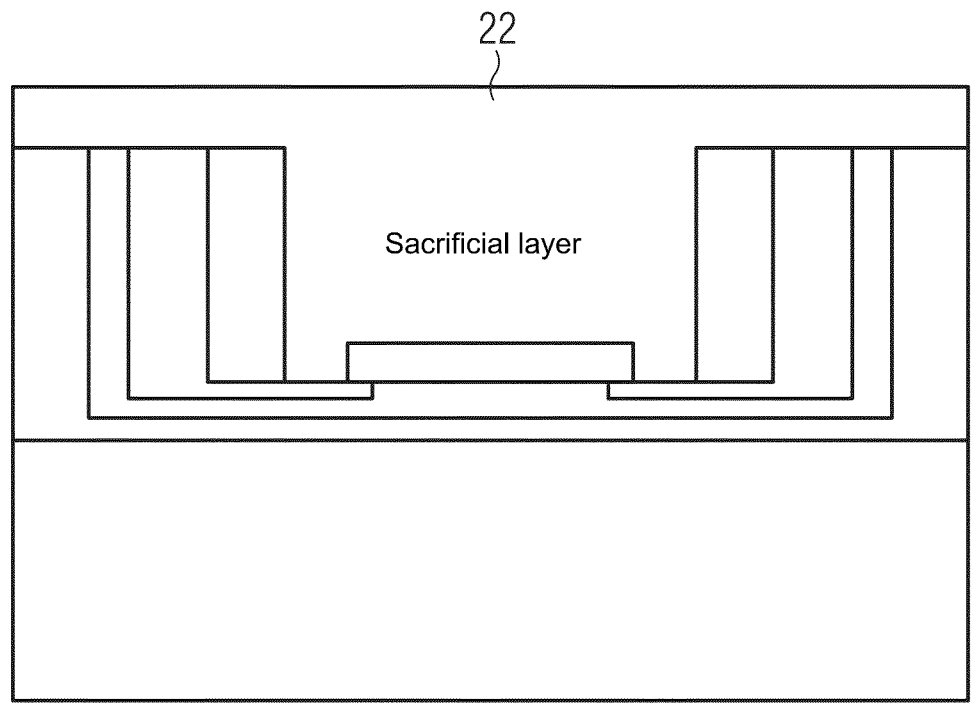
FIGS. 14 to 16 show an alternative method of manufacturing the MEMS gas sensor using a sacrificial layer.
Figure 15:
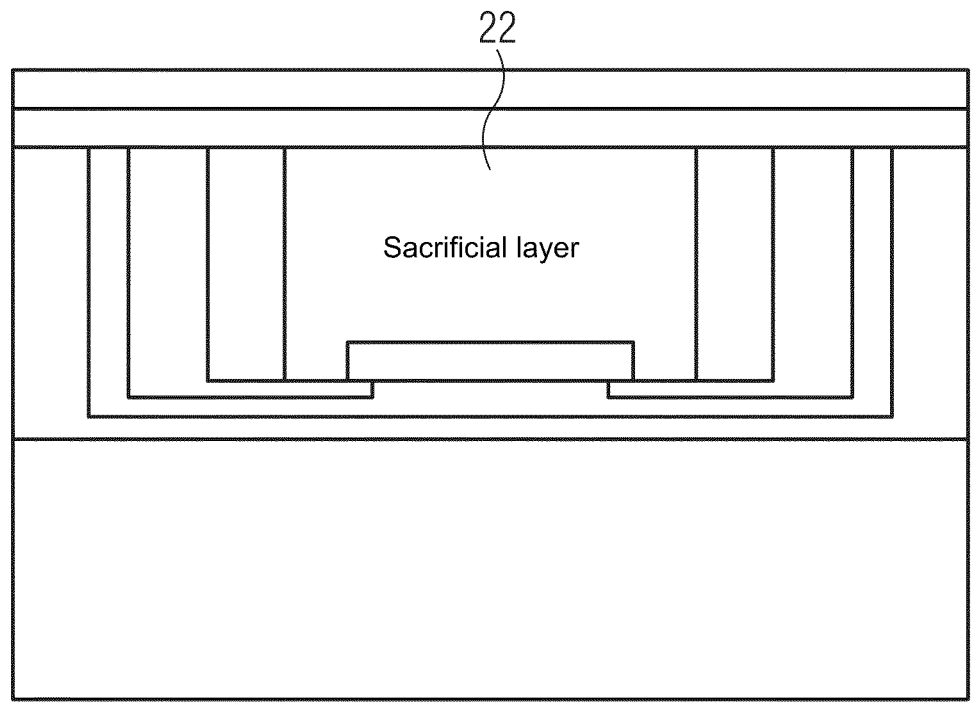
Figure 16:
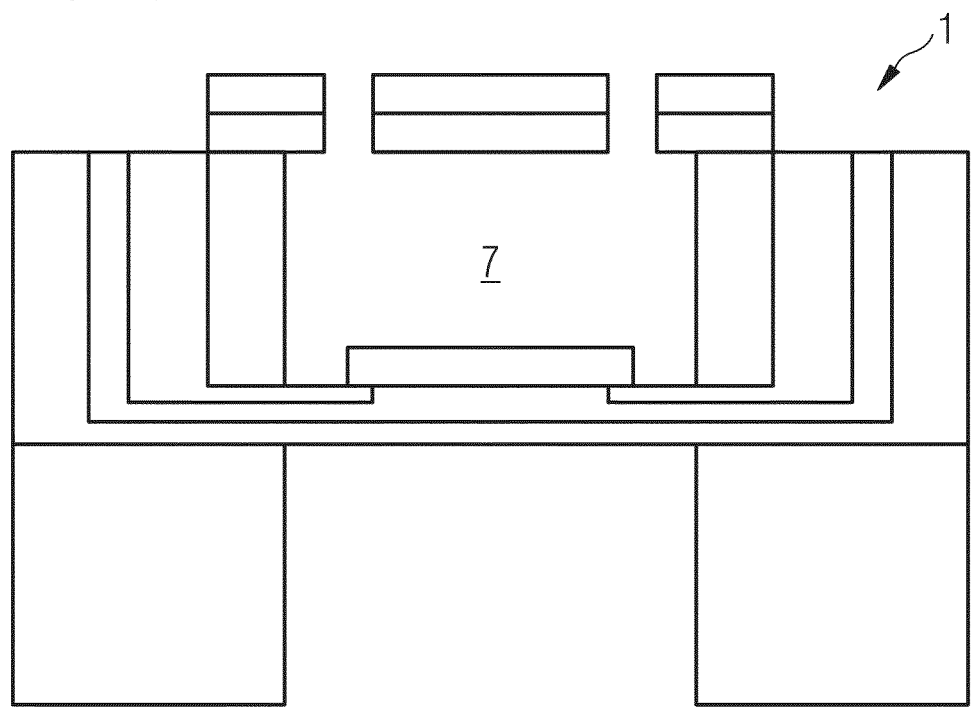

FIGS. 14 to 16 show an alternative method of manufacturing the MEMS gas sensor 1. According to the alternative method, a sacrificial layer 22 is used to form the recess 7 in the carrier 2. The alternative method is also performed on wafer level.

A possible disadvantage of the second manufacturing method is the contact between the gas sensitive element 5 and the sacrificial layer 22 as the sacrificial layer 22 may not be removed completely. In particular there may remain etching residuals. In principle, this should not be a problem as the residuals will be burned when the gas sensitive element 5 is heated to its working temperature during the operation of the MEMS gas sensor 1.

I claim:
1. A MEMS gas sensor comprising:
a carrier having a recess;
a gas sensitive element arranged in the recess; and
a shielding layer at least partially covering the recess,
wherein the shielding layer comprises at least a lower layer facing towards the gas sensitive element and an upper layer facing away from the gas sensitive element,
wherein the shielding layer comprises a middle layer sandwiched between the lower layer and the upper layer, and
wherein the middle layer comprises at least one of aluminum oxide, silicon oxide or titanium.

2. The MEMS gas sensor according to claim 1, wherein the MEMS gas sensor is configured to heat the gas sensitive element.

3. The MEMS gas sensor according to claim 1, wherein the shielding layer is configured to reflect heat emitted by the gas sensitive element.

4. The MEMS gas sensor according to claim 1, wherein the shielding layer is a single layer.

5. The MEMS gas sensor according to claim 1, wherein the lower layer has an absorptance of less than 0.4.

6. The MEMS gas sensor according to claim 1, wherein the lower layer comprises aluminum, silver or palladium.

7. The MEMS gas sensor according to claim 1, wherein the upper layer has an emissivity of less than 0.4.

8. The MEMS gas sensor according to claim 1, wherein the upper layer comprises cadmium, tungsten or bronze.

9. The MEMS gas sensor according to claim 1, wherein the shielding layer is penetrated by ventilation holes.

10. The MEMS gas sensor according to claim 1, wherein the MEMS gas sensor comprises a bottom shielding layer arranged on a side of the carrier facing away from the gas sensitive element.

11. The MEMS gas sensor according to claim 1, wherein the MEMS gas sensor comprises a lateral shielding layer arranged laterally to the gas sensitive element.

12. The MEMS gas sensor according to claim 1, wherein the MEMS gas sensor comprises multiple shielding layers which at least partially cover the recess and which are layered on each other.

13. The MEMS gas sensor according to claim 1, wherein the gas sensitive element is fixed to the carrier by spring arms.

14. A MEMS gas sensor comprising:
a carrier having a recess;
a gas sensitive element arranged in the recess; and
a shielding layer at least partially covering the recess,
wherein the shielding layer comprises at least a lower layer facing towards the gas sensitive element and an upper layer facing away from the gas sensitive element,
wherein the shielding layer comprises a middle layer sandwiched between the lower layer and the upper layer, and
wherein a material of the lower layer is different from a material of the upper layer.

* * * * *